(12) United States Patent
Persson et al.

(10) Patent No.: US 11,559,101 B2
(45) Date of Patent: *Jan. 24, 2023

(54) OUTDOOR POWER EQUIPMENT HEADSET

(71) Applicant: HUSQVARNA AB, Huskvarna (SE)

(72) Inventors: Alexander Persson, Tenhult (SE);
Mattias Karlson, Huskvarna (SE);
Mario D'Ovidio, Cornelius, NC (US);
Jon Funk, Concord, NC (US); Nick Schomer, Charlotte, NC (US)

(73) Assignee: HUSQVARNA AB, Huskvarna (SE)

( * ) Notice: Subject to any disclaimer, the term of this patent is extended or adjusted under 35 U.S.C. 154(b) by 132 days.

This patent is subject to a terminal disclaimer.

(21) Appl. No.: 17/025,064

(22) Filed: Sep. 18, 2020

(65) Prior Publication Data

US 2021/0000211 A1    Jan. 7, 2021

Related U.S. Application Data

(63) Continuation of application No. 15/743,081, filed as application No. PCT/IB2016/054095 on Jul. 7, 2016, now Pat. No. 10,779,603.

(Continued)

(51) Int. Cl.
| | |
|---|---|
| *A42B 3/16* | (2006.01) |
| *H04R 1/10* | (2006.01) |
| *G02B 27/01* | (2006.01) |
| *A42B 3/04* | (2006.01) |
| *A61F 11/14* | (2006.01) |
| *G10K 11/178* | (2006.01) |

(52) U.S. Cl.
CPC .............. *A42B 3/166* (2013.01); *A42B 3/042* (2013.01); *A61F 11/14* (2013.01); *G02B 27/017* (2013.01); *G10K 11/17823* (2018.01); *G10K 11/17873* (2018.01); *H04R 1/1083* (2013.01); *A61F 11/145* (2022.01); *G02B 2027/014* (2013.01); *G02B 2027/0141* (2013.01); *G02B 2027/0187* (2013.01); *G10K 11/17837* (2018.01); *G10K 11/17885* (2018.01); *G10K 2210/1081* (2013.01); *H04R 2460/01* (2013.01)

(58) Field of Classification Search
CPC .. A42B 3/166; G10K 11/17823; F21V 21/084
USPC ....................................................... 2/423, 428
See application file for complete search history.

(56) References Cited

U.S. PATENT DOCUMENTS

| | | | |
|---|---|---|---|
| 4,797,736 A | * | 1/1989 | Kloots .................. F21V 21/084 348/370 |
| 5,991,085 A | | 11/1999 | Rallison et al. |

(Continued)

FOREIGN PATENT DOCUMENTS

| | | |
|---|---|---|
| EP | 2661097 A2 | 11/2013 |
| WO | 2015006784 A2 | 1/2015 |

OTHER PUBLICATIONS

International Search Report and Written Opinion for International Application No. PCT/IB2016/054095 dated Oct. 10, 2016.

(Continued)

*Primary Examiner* — Timothy K Trieu
(74) *Attorney, Agent, or Firm* — Burr & Forman LLP

(57) ABSTRACT

A headset apparatus configured to be worn by a user operating outdoor power equipment. The headset may include a noise cancelling system and/or enhanced glasses.

17 Claims, 5 Drawing Sheets

Related U.S. Application Data

(60) Provisional application No. 62/190,793, filed on Jul. 10, 2015.

(56) References Cited

U.S. PATENT DOCUMENTS

| | | |
|---|---|---|
| 10,425,718 B2 | 9/2019 | Cha et al. |
| 2005/0101439 A1 | 5/2005 | Berger |
| 2008/0130271 A1* | 6/2008 | Harris ................. A42B 3/0406 |
| | | 362/105 |
| 2008/0159553 A1 | 7/2008 | Copley et al. |
| 2011/0047668 A1 | 3/2011 | Manzella, Jr. et al. |
| 2011/0197327 A1* | 8/2011 | McElroy ................. A42B 3/32 |
| | | 2/2.5 |
| 2013/0061376 A1 | 3/2013 | Halfaker |
| 2014/0352037 A1 | 12/2014 | VanDerWoude et al. |
| 2014/0362446 A1 | 12/2014 | Bickerstaff et al. |
| 2015/0343294 A1 | 12/2015 | Leech et al. |
| 2016/0349835 A1 | 12/2016 | Shapira |
| 2017/0035139 A1 | 2/2017 | Weatherby et al. |
| 2017/0142507 A1 | 5/2017 | Chang et al. |
| 2019/0075879 A1* | 3/2019 | Persson ................. A61F 11/14 |

OTHER PUBLICATIONS

International Preliminary Report on Patentability for International Application No. PCT/IB2016/054095 dated Jan. 16, 2018.

\* cited by examiner

OUTDOOR POWER EQUIPMENT HEADSET

BACKGROUND

Currently, outdoor power equipment is used by consumers to perform various tasks, such as mowing using a lawn mower or cutting down a tree with a chainsaw. However, when using outdoor power equipment, the outdoor power equipment can be quite loud, thereby lowering the user's experience with the outdoor power equipment.

Additionally, when performing tasks using the outdoor power equipment, the user may not know of certain obstacles, terrain or be aware of other items relating to the outdoor power equipment or the surrounding areas thereof while in use.

By having these disadvantages as part of the user's experience with the outdoor power equipment, the user may be less inclines to use the outdoor power equipment or may not have as an optimal experience with the outdoor power equipment.

SUMMARY OF INVENTION

The present application solves one or more of the above disadvantages of the outdoor power equipment. In this regard, the present application describes a headset that may be worn by the user during use of the user's outdoor power equipment. The headset may have (1) active noise cancellation and/or (2) enhanced glasses.

A headset apparatus configured to be worn by a user operating outdoor power equipment. The headset may include a noise cancelling system and/or enhanced glasses. The noise cancelling system may include an eye covering device configured to cover at least a portion of an eye of the user; a display that outputs an image on the eye covering device so that the user perceives the image; an optical device that receives optical information based on the position of the eye covering device of the surroundings of the user; a processor that outputs information to the display. The enhanced glasses may be configured to be worn by a user operating outdoor power equipment, the enhanced glasses may include an ear covering device to cover at least a portion the user's ear while the user operated the outdoor power equipment, wherein the ear covering device is in electrical communication or is in wireless communications with the outdoor power equipment; a device to receive noise information outputted by a signal from the outdoor power equipment; and a processor that receives the signal from the outdoor power equipment and provides noise that cancels with noise identified from the outdoor power equipment.

BRIEF DESCRIPTION OF DRAWINGS

Aspects of the present invention is further described in the detailed description which follows in reference to the noted plurality of drawings by way of non-limiting examples of embodiments of the present invention in which like reference numerals represent similar parts throughout the several views of the drawings and wherein.

DETAILED DESCRIPTION

Various embodiments of the present application are described below. However, prior to discussing the various embodiments and details, a general overview of the headset is provided below.

General Overview

Figure 1:
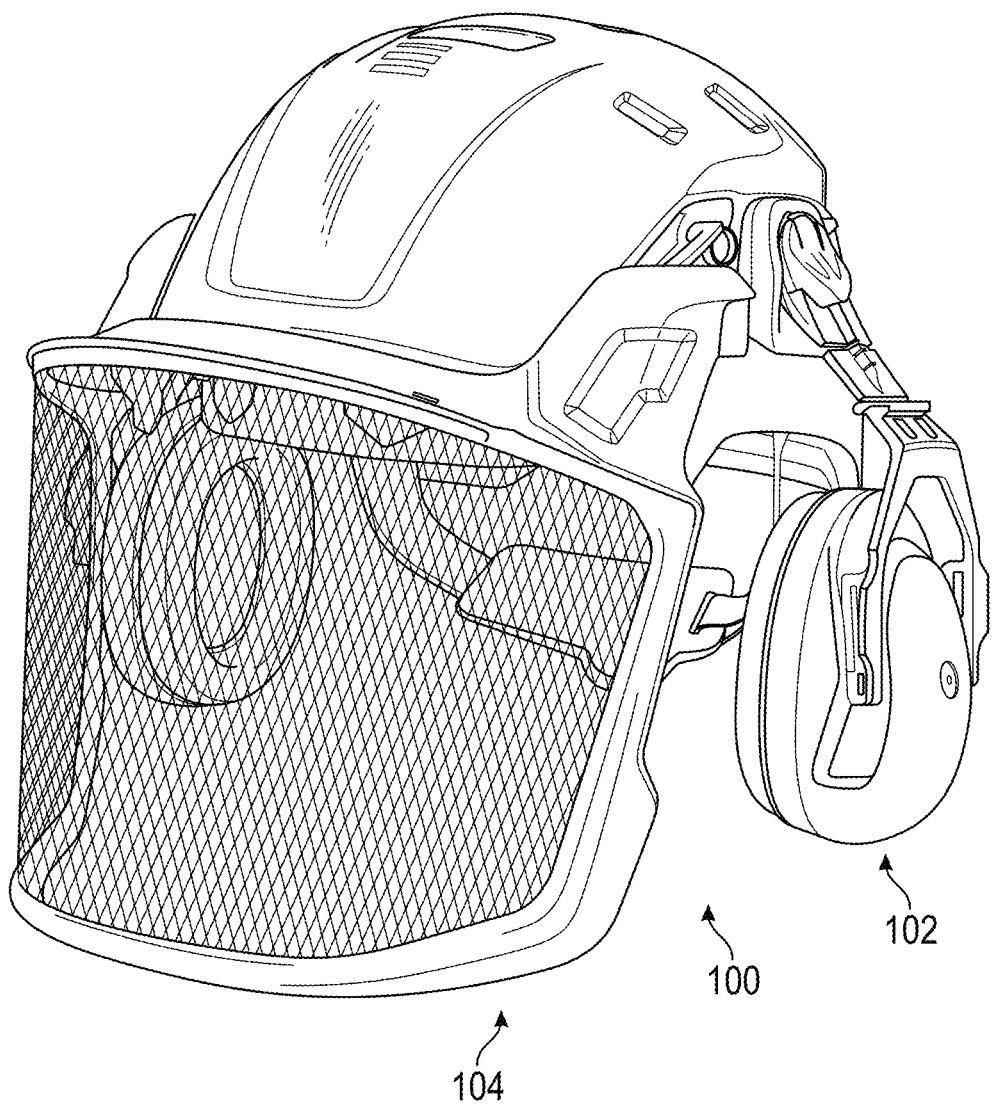
FIG. 1 illustrates a headset with both noise cancellation and a shield in according with one embodiment.
Figure 2:
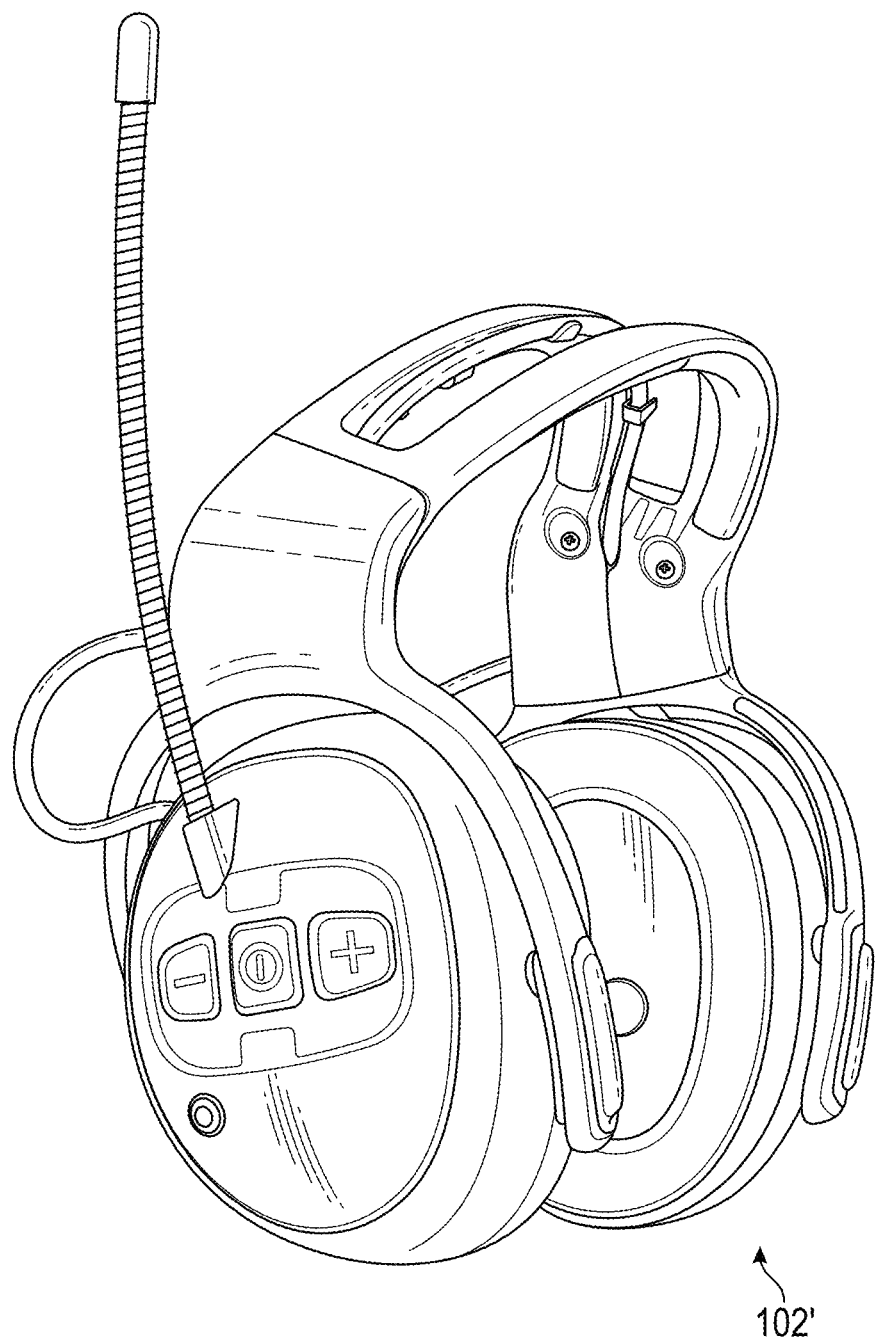
FIG. 2 illustrates a headset with just the noise cancelling feature in according with one embodiment.

FIG. 1 illustrates an exemplary headset 100. As shown, the headset may include an active noise cancellation system 102 and enhanced glasses 104. Alternatively, the headset may include only an active noise cancellation system 102 or enhanced glasses 104. For example, FIG. 2 shows only an active noise cancellation system 102'.

The headset 100 is configured to be worn on the head of a user of outdoor power equipment or tool. It should be understood that the headset 100 works in tandem with the user's outdoor power equipment so that the headset is in direct communication with the user's outdoor power equipment.

As mentioned above, the headset may have, in some embodiments, an active noise cancellation system. The active noise cancellation system may be connected with an outdoor power equipment, such as a tool (e.g., chain saw, lawn mower, string trimmer, etc.), and may be automatically activated when the tools gets activated. Noise cancellation could be improved if the sound spectrum of each individual tool (or each type of tool) is stored in a database so that the noise cancellation algorithm could individually adopted. Noise cancellation might only be active within a certain frequency spectrum that is associated with a noise level of high volume (e.g., high engine speed) so that at other times (e.g., an engine in idle speed) no noise cancelation will be active to allow for better acoustics and improved comfort.

Also, as mentioned above, the headset may include enhanced glasses, face/eye shield, or the like and may be included or not included along with the active noise cancellation system. The enhanced glasses may provide various information to the user when using the outdoor power equipment, including certain notifications, general operational information relating to the outdoor power equipment, warnings, and other audio/visual indications. This information may be stored in memory, manually input, automatically collected by sensors, automatically processed by microprocessor on tractor, etc.

Headset

Figure 3:
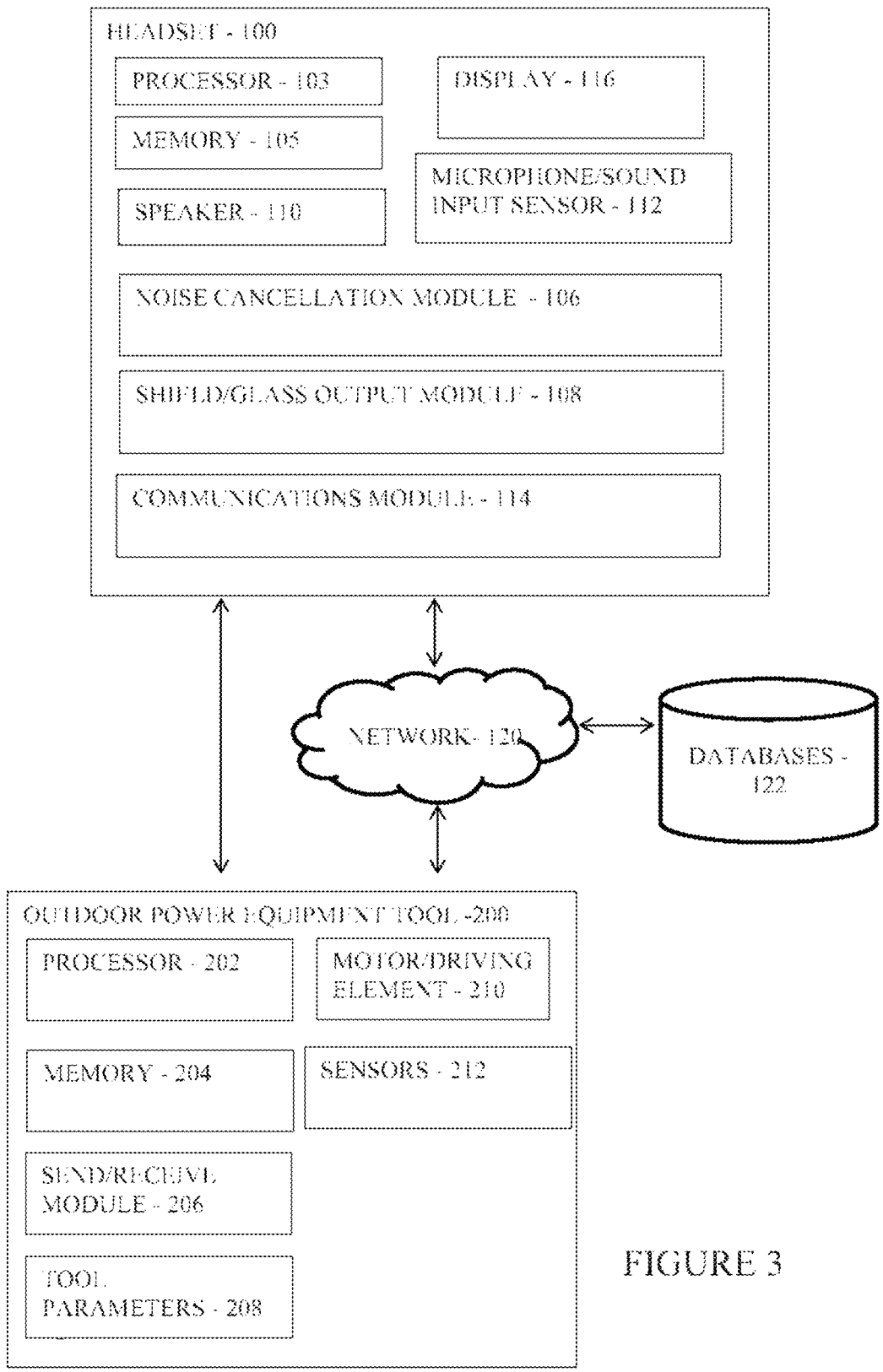
FIG. 3 illustrates a headset system in according with some embodiments.
Figure 4:
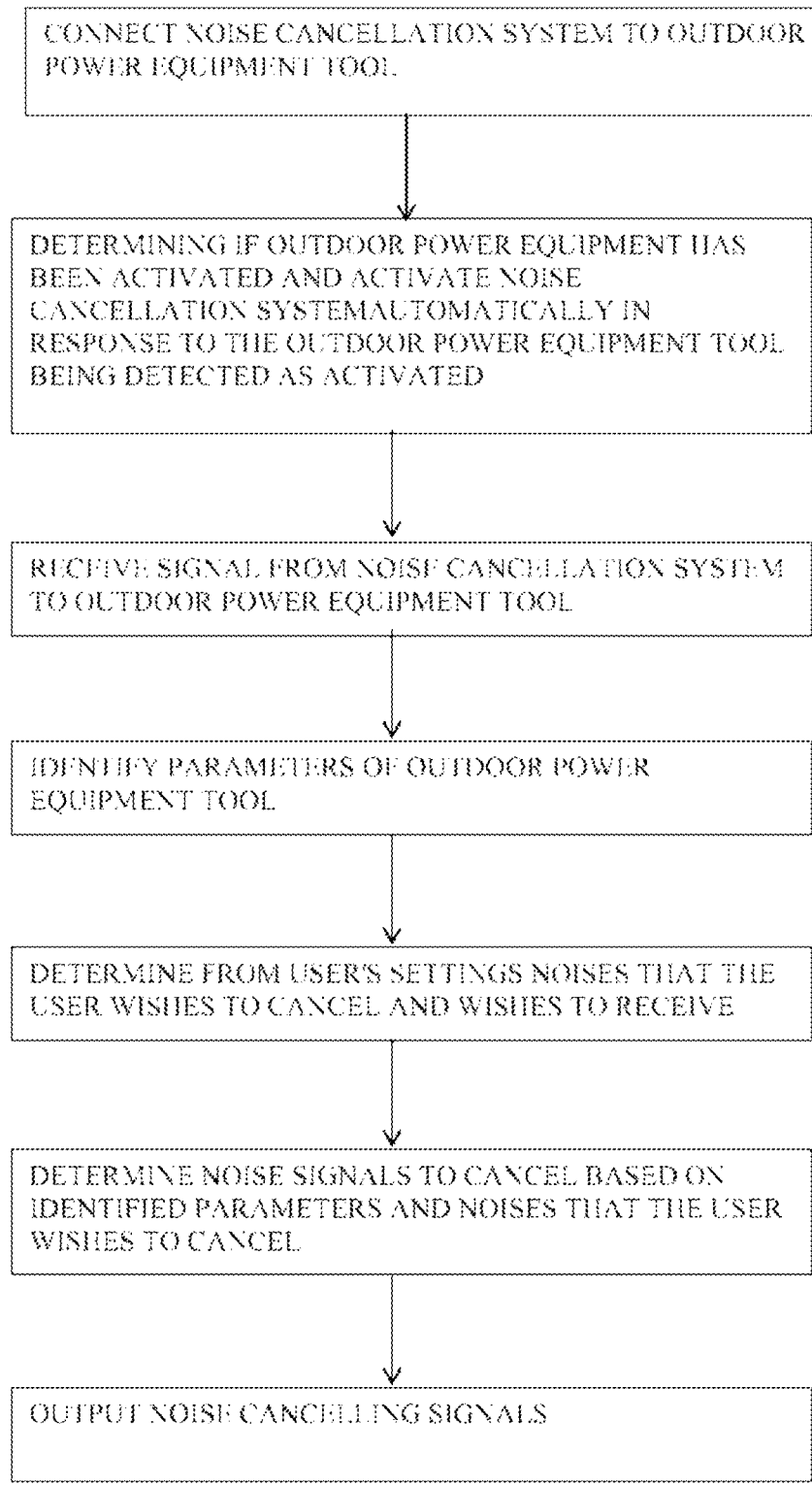
FIG. 4 illustrates a method of operation of the noise cancelling system in according with one embodiment.
Figure 5:
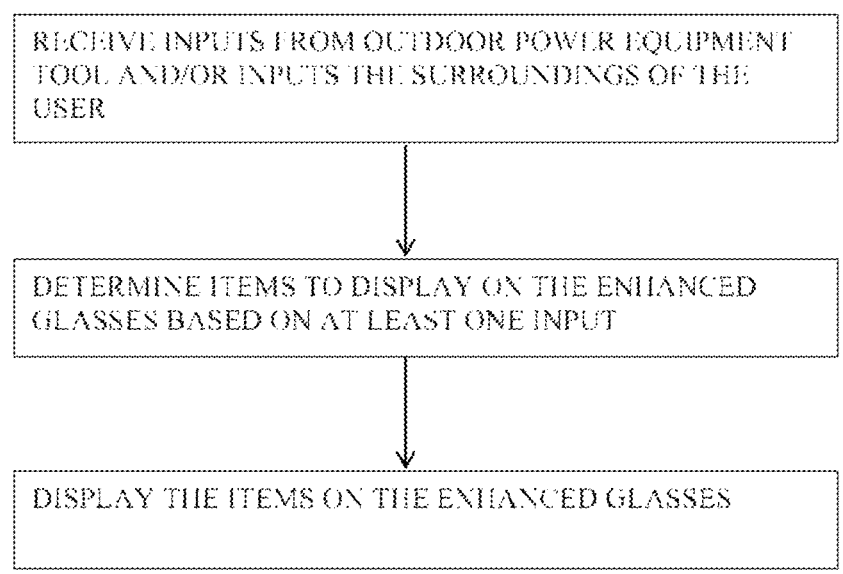
FIG. 5 illustrates a method of operation of the noise cancelling system in according with one embodiment.

Referring back to FIG. 1 as well in FIG. 3, the headset may be in communication with the user's outdoor power equipment (also referred to herein as an "outdoor power equipment tool" or just "tool") that is in operation. The headset may be in communication with the user's outdoor power equipment in any way, such as by wireless communication systems (including short range communications, such as Bluetooth) or by wired communication systems (e.g., a wire that plugs into the outdoor power equipment).

The headset 100 may be configured to receive one or more data signals from the outdoor power equipment and also may be configured to receive audio signals from the outdoor power equipment using the microphone 112.

The headset 100 may have one or more processors 103 and memory 105 to process signals received and output data, such as displaying data on the glasses display 116, receiving noise feedback from the tool via a microphone 112 or outputting audio to speakers 110 of the noise cancellation system.

The outdoor power equipment tool 200 may include a processor 202 and memory 204.

The processors 103, 202 of the headset and/or the outdoor power equipment tool may be configured to perform one or more functions of the methods described herein. One or more functions may be performed using any of the processors and the present invention should not be limited to any one processor performing all of the functions described herein, although one of the processors may be configured to performed all of the functions discussed herein in one embodiment. Accordingly in one embodiment, the processor and/or memory may be located on the outdoor power equipment and as such, the processing (including receiving, outputting, determining, etc.) may be performed at the outdoor power equipment. In another embodiment, at least one processor and memory may be located on both the headset 100 and the outdoor power equipment and processing can be performed on either or both of the headset and/or outdoor power equipment.

The headset includes a communication module which facilitates transmitting and receiving of communications between the headset and the tool 200.

The headset may include a noise cancellation module 106 which is operable on the noise cancellation system, discussed below. The headset may include a shield/glass output module 108 which is operable on the enhanced glass system, both of which are discussed below.

NOISE CANCELLATION SYSTEM

The noise cancellation system may be implemented as part of the headset. In one embodiment, the noise cancellation system is a set of earmuffs, earbuds, or other system which connects to the user's ears so that the sound may be directly provided from the noise cancellation system to the user's ears.

The active noise cancellation system is electrically and/or mechanically connected with an outdoor power equipment tool (e.g., chain saw, lawnmower, etc.) and is automatically activated when the tool may be activated or turned on or when a noise level has reached a predetermined threshold.

When the tool is activated, the tool may send a signal to the noise cancellation system identifying the identity of the tool and/or parameters of noise of the tool. For example, the outdoor power equipment tool may be a model XY chainsaw and a computing device in the model XY chainsaw may send an identification signal from the chainsaw to the noise cancellation system with a message parameter or header in the message indicating "model XY chainsaw" and/or "noise level X," "frequency level Y." Other information about current operations of the chainsaw may also be sent instantaneously and continuously from the chainsaw to the noise cancellation system, including the type of motor in the chainsaw, the current RPM, or whether there are other parts of the tool which may cause noise (e.g., movement of the chain of the chainsaw) in addition to the motor, or other information that cause noise of the chainsaw.

In response to the noise cancellation system receiving such information from the chainsaw, the noise cancellation system may determine noises and noise levels that the outdoor power equipment tool is currently making or is capable of making. In this regard, the noise cancellation system creates a noise cancellation algorithm based on the noise data received from the signal sent from the chainsaw to the noise cancellation system.

The sound spectrum of each individual tool (or each type of tool) may be stored in a database so that the noise cancellation algorithm could individually adopted relative to each tool or type of tool. Noise cancellation might only be active within a certain frequency spectrum that is associated with a noise level of high volume (e.g., high engine speed) so that at other times (engine in idle speed) no noise cancelation will be active to allow for better acoustics and improved comfort.

It should be understood that the signal to the noise cancellation system from outdoor power equipment tool (e.g., chainsaw) indicating that the tool starts and an identity of the machine may be used by the noise cancellation system to identify noise that is dangerous to an operation of the tool and noise that the user may desire to hear or noise that is not dangerous. In this regard, the noise cancellation system can filter out the dangerous noise but keep the noise of the outdoor power equipment (e.g., the chain going around), such as what is RPM, what is frequency, etc., according to some embodiments. In another embodiment, the noise cancellation system could completely block all sounds by insulating the ears from the noise.

The noise cancellation system may be configured to identify the noises that are or will be output by the outdoor power equipment tool the user is operating and the noise cancellation system may output cancelling noise based on the identified noises of the tool. In this regard, the cancelling noise and the identified noises would combine together and would then cancel each other out so that the combination thereof would result is no noise at all. It should be noted that only some of the noises of a plurality of the identified noises may be cancelled, thereby allowing the noise cancellation system to selectively cancel only some noises of the identified noises. However, as mentioned above, in one embodiment, the cancelled noises could correspond to all identified noises so that all noises received are cancelled so substantially no noise is received by the users ear.

It should be understood that the noise cancellation system may be part of the headset that the user wears and may directly cover all or at least a portion of the users ear canal. The noise cancellation system, in this regard, is separate from the outdoor power equipment tool. Thus, the noise cancellation system of the headset may be an accessory to the outdoor power equipment tool.

As mentioned above, the noise cancellation system may be activated by activation of a portion of the outdoor power equipment tool or by the noise level of the outdoor power equipment tool exceeding a predetermined noise threshold or a predetermine threshold parameter of the outdoor power equipment tool. For example, the noise cancellation system that is connected to a chainsaw may automatically be activated by movement of the chainsaw trigger that activates the chain movement of the chainsaw or may be activated by recognizing an RPM level of the outdoor power equipment tool.

The noise cancellation system may be connected to the outdoor power equipment tool by a wired connection (e.g., plugging in a wire that connects the processor and memory of the noise cancellation system with the tool) or by a wireless connection (e.g., short range wireless, such as Bluetooth, WIFI, or RFID wireless connection) to the outdoor power equipment tool. The wireless connection may be directly connected between the noise cancellation system and the outdoor power equipment tool or may be connected over a network using the wireless connection.

The noise cancellation system may send out a noise cancellation signal to cancel the noise cancellation signal. This may be done in a multitude of ways. For example, the noise cancellation system could record the current sound (e.g., frequency, sound level, etc.) and use that sound as the noise cancellation signal to cancel the current noise being generated by the outdoor power equipment tool.

In another embodiment, the manufacturer could have a predefined signal that the noise cancellation system uses to cancel the noise. For example, a manufacturer would know certain parameters about the outdoor power equipment tool (e.g., the RPM level, frequency, etc. in chainsaw) and save the noise cancellation signal in the noise cancellation system for noise cancelling when the outdoor power equipment tool is later in use. This can be done since the manufacturer will basically know what the noise signal will be prior to the noise signal actually being generated.

The noise cancellation system may be included in any apparatus, such as helmet, ear plugs (with wires), wireless ear buds/plugs, earmuffs, or any other system which would cover at least a portion of a user's ear holes.

Enhanced Glasses

The enhanced glasses may include enhanced safety glasses, face/eye shield (trimmers or chainsaws), or other augmented reality headset that can be used when operating the outdoor power equipment. The enhanced glasses are placed between the user's eyes and items and objects where the operator views.

The enhanced glasses has a display 116 which may displays from the processor 103 using the noise cancellation module 106 a visualization of where items should operate the tool or items to avoid. For example, it may show an user's wife's flowers to avoid, other obstacles (e.g., rocks, golf balls, etc.), where sprinkler heads are located, when sprinkler heads are about to come on, whether the user's engine load is too high, that the user is approaching a high engine load area of the user's yard (i.e., thick grass), upcoming terrain to prepare the user for a slope, show the user how to approach/drive into the slope, how to stripe the user's yard to achieve a particular pattern (football logo, happy birthday, etc.), incoming calls, or seeing the optimal operation route.

This information may be stored in the headset memory 105, manually input, automatically collected by sensors 212, automatically processed by microprocessor on the tool, etc. The information could be used to show the user what the user actually did already (e.g., where the user has mowed, which trees have been cut down, etc.) and what the still needs to do (e.g., where the user still needs to mow, which premarked trees still need cutting). This may be especially helpful when the operator is mowing, for example, since some of the uncut area may be hidden by grass discharge. Thus, the glasses can show the user where he has cut and where the user has not yet cut.

This methodology could also be applied to areas you have fertilized and show you which areas still need fertilization.

The headset's microphone/sound input sensor may "hear" when someone is calling the user's name/sound discrepancy and the resulting output/notification to the operator may be visual. The headset may transform aural inputs (e.g., spacial inputs, such as trees, display a map, etc.) detected from the microphone or the visual inputs to visual outputs. In this regard, the system does not need to go through the outdoor power equipment tool (e.g., tractor) or talk to the outdoor power equipment (e.g., tractor).

The glasses may display various indicators such as lawn outdoor power equipment tool specific outputs (e.g., fuel, oil levels, etc.) and/or inputs (e.g., if a mower on a too high of a slope, the user could shut down or control machine, etc.). In this regard, the glasses do not need to be tied to a headset, but instead could be on a smartphone, or could be on your outdoor power equipment's screen.

The glasses may recognize problems and address them for the user. For example, if there is something going wrong with the user's chainsaw the headset may display "please stop cutting the tree" based on dieseling of chainsaw. This is could be part of the noise cancellation system (earmuffs, for example) or could be part of just the enhanced glasses.

The glasses may include a heads up display i, for example, the upper right hand corner (e.g., to should how much fuel left, how long the mower has been in use, etc.).

The glasses may include augmented reality whatever the user's sees in front of you, it then says "go this way"—stand back, measure the tree with your glasses. The glasses may calculate the tree parameters and says this is where you should cut the tree based on the angle, for example. It could be built into the tool (chainsaw, tractor, mower, etc.), could use phone (via wireless), or could be part of the earmuffs, or could be tethered pack in the user's pocket.

The glasses calculate ideal path based on parameters measured, such as slope, obstacles (sprinklers), weight of the machine, the user's weight, sprinklers (where the headset connects with sprinkler system to determine if sprinklers are up, etc.). The glasses could connect with device that identifies animated objects and notify user of glasses where these people are located.

It should be understood that the glasses and/or noise cancellation system may be implemented on any outdoor power equipment, and the discussion of using such systems on a chainsaw, tractor or mower, as discussed herein are merely used for illustrative purposes. The tools that the glasses and/or noise cancellation system should not be limited to any particular tool or category of tools.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to embodiments of the invention in the form disclosed. Many modifications and variations will be apparent to those of ordinary skill in the art without departing from the scope and spirit of embodiments of the invention. The embodiment was chosen and described in order to best explain the principles of embodiments of the invention and the practical application, and to enable others of ordinary skill in the art to understand embodiments of the invention for various embodiments with various modifications as are suited to the particular use contemplated.

Although specific embodiments have been illustrated and described herein, those of ordinary skill in the art appreciate that any arrangement which is calculated to achieve the same purpose may be substituted for the specific embodiments shown and that embodiments of the invention have other applications in other environments. This application is intended to cover any adaptations or variations of the present invention. The following claims are in no way intended to limit the scope of embodiments of the invention to the specific embodiments described herein.

What is claimed is:

1. A headset apparatus configured to be worn by a user operating outdoor power equipment, the headset apparatus comprising:
   an eye covering device configured to cover at least a portion of an eye of the user;
   a display that outputs an image on the eye covering device to permit the user to perceives the image;
   a sensor configured to detect optical information indicating a current position and current view direction of the eye covering device relative to environmental surroundings of the headset apparatus; and
   a processor, in communication with the outdoor power equipment, configured to:
      retrieve, from a storage memory, avoidance information, the avoidance information indicating a location of an area to avoid using the outdoor power equipment;
      receive the optical information from the sensor;
      receive an operational parameter from the outdoor power equipment;
      determine, based on the optical information and avoidance information, a first portion of the environmental surroundings located at the area to avoid where the user should avoid operating the outdoor power equipment; and
      output, based on the current position of the eye covering device relative to the environmental surroundings, the image to the display, the image including an indication of the operational parameter of the outdoor power equipment and an augmented reality visualization of the first portion of the environmental surroundings superimposed over the environmental surroundings at the location of the area to avoid to permit the user to identify and avoid using the outdoor power equipment in the area to avoid.

2. The headset apparatus of claim 1, wherein the eye covering device comprises glasses that are at least partially see-through.

3. The headset apparatus of claim 1, wherein the operational parameter of the outdoor power equipment is a value measured and communicated by the outdoor power equipment, the operational parameter being one of revolutions per minute (RPM) of a motor of the outdoor power equipment, a fuel level of the outdoor power equipment, or an oil level of the outdoor power equipment.

4. The headset apparatus of claim 1, wherein the processor is further configured to:
   receive an alert relating to the operational parameter of the outdoor power equipment; and
   output the image to the display with a warning associated with the operational parameter and the augmented reality visualization.

5. The headset apparatus of claim 1, wherein the headset apparatus communicates via short range wireless communication with the outdoor power equipment.

6. The headset apparatus of claim 1, wherein the augmented reality visualization of the first portion of the environmental surroundings includes an indication of a location of a sprinkler head.

7. An apparatus configured to be worn by a user operating outdoor power equipment, the apparatus comprising:
   a headset;
   a display mounted to the headset and visible to the user such that the display moves with the user's head, the display being configured to output an image;
   a sensor configured to detect optical information indicating a current position and current view direction of the headset relative to environmental surroundings of the headset; and
   a processor, in communication with the outdoor power equipment, configured to:
      retrieve, from a storage memory, avoidance information, the avoidance information indicating a location of an area to avoid using the outdoor power equipment;
      receive the optical information from the sensor;
      receive an operational parameter from the outdoor power equipment;
      determine, based on the optical information and avoidance information, a first portion of the environmental surroundings located at the area to avoid where the user should avoid operating the outdoor power equipment; and
      output, based on the current position of the eye covering device relative to the environmental surroundings, the image to the display, the image including an indication of the operational parameter of the outdoor power equipment and an augmented reality visualization of the first portion of the environmental surroundings superimposed over the environmental surroundings at the location of the area to avoid to permit the user to identify and avoid using the outdoor power equipment in the area to avoid.

8. The apparatus of claim 7, wherein the image is displayed so that at least a part of a user's vision is not obstructed by the image.

9. The apparatus of claim 7, wherein the operational parameter of the outdoor power equipment is a value measured and communicated by the outdoor power equipment, the operational parameter being one of revolutions per minute (RPM) of a motor of the outdoor power equipment, a fuel level of the outdoor power equipment, or an oil level of the outdoor power equipment.

10. The apparatus of claim 7, wherein the processor is further configured to:
- receive an alert relating to the operational parameter of the outdoor power equipment; and
- output the image to the display with a warning associated with the operational parameter and the augmented reality visualization.

11. The apparatus of claim 7, wherein the headset apparatus communicates via short range wireless communication with the outdoor power equipment.

12. The apparatus of claim 7, wherein the augmented reality visualization of the first portion of the environmental surroundings includes an indication of a location of a sprinkler head.

13. A method for operating a headset apparatus configured to be worn by a user operating outdoor power equipment, the method comprising:
- retrieving, by a processor of the headset apparatus from a storage memory, avoidance information, the avoidance information indicating a location of an area to avoid using the outdoor power equipment;
- receiving optical information from a sensor of the headset apparatus, the sensor being configured to detect the optical information which indicates a current position and current view direction of an eye covering device relative to environmental surroundings of the headset apparatus, the eye covering device being configured to cover at least a portion of an eye of the user:
- receiving an operational parameter from the outdoor power equipment via a communication with a processor of the headset apparatus;
- determining, by the processor of the headset apparatus and based on the optical information and avoidance information, a first portion of the environmental surroundings located at the area to avoid where the user should avoid operating the outdoor power equipment; and
- outputting, to a display on the eye covering device of the headset apparatus and based on the optical information and avoidance information, an image including an indication of the operational parameter of the outdoor power equipment and an augmented reality visualization of the first portion of the environmental surrounding s superimposed over the environmental surroundings at the location of the area to avoid to permit the user to identify and avoid using the outdoor power equipment in the area to avoid.

14. The method of claim 13, wherein the eye covering device comprises glasses that are at least partially see-through.

15. The method of claim 13, wherein the operational parameter of the outdoor power equipment is a value measured and communicated by the outdoor power equipment, the operational parameter being one of revolutions per minute (RPM) of a motor of the outdoor power equipment, a fuel level of the outdoor power equipment, or an oil level of the outdoor power equipment.

16. The method of claim 13 further comprising:
- receiving an alert relating to the operational parameters of the outdoor power equipment; and
- outputting the image to the display with a warning associated with the operational parameter and the augmented reality visualization.

17. The method of claim 13, wherein the processor of the headset apparatus communicates via short range wireless communication with the outdoor power equipment.

* * * * *